United States Patent
Mathis et al.

[11] Patent Number: 6,037,281
[45] Date of Patent: Mar. 14, 2000

[54] CLOTH-LIKE, LIQUID-IMPERVIOUS, BREATHABLE COMPOSITE BARRIER FABRIC

[75] Inventors: Michael Peter Mathis, Marietta; Ann Louise McCormack, Cumming; Daniel Kenneth Schiffer, Marietta, all of Ga.

[73] Assignee: Kimberly-Clark Worldwide, Inc., Neenah, Wis.

[21] Appl. No.: 08/777,365

[22] Filed: Dec. 27, 1996

[51] Int. Cl.$^7$ .................................................. B32B 27/12
[52] U.S. Cl. ......................... 442/394; 442/398; 442/382; 428/315.5; 428/315.9
[58] Field of Search ................................... 442/394, 382, 442/398; 428/315.5, 315.9, 316.6

[56] References Cited

U.S. PATENT DOCUMENTS

| | | | |
|---|---|---|---|
| 1,741,530 | 12/1929 | Mayer | 154/124 |
| 2,971,322 | 2/1961 | Bouvet | 57/140 |
| 3,047,444 | 7/1962 | Harwood | 154/46 |
| 3,059,313 | 10/1962 | Harmon | 28/80 |
| 3,256,258 | 6/1966 | Herrman | 260/93.7 |
| 3,338,992 | 8/1967 | Kinney | 264/24 |
| 3,341,394 | 9/1967 | Kinney | 161/72 |
| 3,396,071 | 8/1968 | Couzens | 161/150 |
| 3,406,033 | 10/1968 | Reitz | 117/7 |
| 3,438,844 | 4/1969 | Kumin | 161/150 |
| 3,485,695 | 12/1969 | Ness | 156/229 |
| 3,502,538 | 3/1970 | Petersen | 161/150 |
| 3,542,615 | 11/1970 | Dobo et al. | 156/181 |
| 3,575,784 | 4/1971 | Phillips et al. | 161/150 |
| 3,692,618 | 9/1972 | Dorschner et al. | 161/72 |
| 3,772,417 | 11/1973 | Vogt | 264/230 |
| 3,802,817 | 4/1974 | Matsuki et al. | 425/66 |
| 3,932,682 | 1/1976 | Loft et al. | 428/296 |
| 3,949,128 | 4/1976 | Ostermeier | 428/152 |
| 4,013,816 | 3/1977 | Sabee et al. | 428/288 |
| 4,041,203 | 8/1977 | Brock et al. | 428/157 |
| 4,047,534 | 9/1977 | Thomaschefsky et al. | 128/461 |
| 4,125,114 | 11/1978 | Repke | 128/280 |
| 4,147,827 | 4/1979 | Breidt, Jr. et al. | 428/218 |

(List continued on next page.)

FOREIGN PATENT DOCUMENTS

| | | | |
|---|---|---|---|
| 0 019 295 | 5/1980 | European Pat. Off. | D06C 7/02 |
| 0 030 418 | 6/1981 | European Pat. Off. | D04H 1/74 |
| 0 105 629 | 4/1984 | European Pat. Off. | B29C 67/20 |
| 0 127 483 | 12/1984 | European Pat. Off. | D04H 1/54 |
| 0 180 703 | 4/1985 | European Pat. Off. | D06C 7/02 |
| 0 227 481 | 7/1987 | European Pat. Off. | C08J 5/18 |
| 0 237 642 | 9/1987 | European Pat. Off. | F26B 21/06 |
| 0 434 115 | 6/1991 | European Pat. Off. | |
| 0 444 671 | 9/1991 | European Pat. Off. | C08F 297/08 |
| 0 505 027 | 9/1992 | European Pat. Off. | D04H 13/00 |
| 0 549 954 | 7/1993 | European Pat. Off. | A41D 31/00 |
| 0 554 896 | 8/1993 | European Pat. Off. | B32B 27/12 |
| 2205407 | 11/1972 | France | B29F 3/00 |
| 20 46 593 | 11/1971 | Germany . | |
| 14 60 514 | 3/1977 | Germany . | |
| 27 57 526 | 6/1979 | Germany | D06C 7/00 |
| 26 32 875 | 1/1982 | Germany | D04H 1/48 |
| 34 38 859 | 7/1985 | Germany | D06C 7/02 |
| 26 13 963 | 1/1986 | Germany | D06C 7/00 |
| 37 24 510 | 2/1989 | Germany | D06N 7/00 |
| 91-097459 | 4/1991 | Japan | A61F 13/54 |
| 4-227260 | 8/1992 | Japan | A61F 13/15 |
| 1 217 498 | 12/1970 | United Kingdom | D01D 5/00 |
| 1 308 904 | 3/1973 | United Kingdom | D06C 27/00 |
| 1 399 666 | 7/1975 | United Kingdom | D06C 3/02 |
| 1 532 467 | 11/1978 | United Kingdom | D06C 7/00 |
| 2 027 637 | 2/1980 | United Kingdom | B01D 13/04 |
| 1 575 972 | 10/1980 | United Kingdom | D06C 7/02 |
| 1 576 436 | 10/1980 | United Kingdom | D04H 13/00 |
| 2 149 720 | 6/1985 | United Kingdom | B32B 31/18 |
| 2 175 026 | 11/1986 | United Kingdom | D04H 1/54 |
| 2 290 052 | 12/1995 | United Kingdom | B32B 27/12 |
| 2 296 216 | 6/1996 | United Kingdom | B32B 27/12 |
| 94/04606 | 3/1994 | WIPO | C08K 3/00 |

*Primary Examiner*—Daniel Zirker
*Attorney, Agent, or Firm*—William D. Herrick

[57] ABSTRACT

The present invention is directed to cloth-like, liquid-impervious, breathable composite barrier fabrics. More particularly, the present invention is directed to cloth-like, liquid-impervious, breathable film-nonwoven composite fabrics having biological liquid barrier capabilities for use as, for example, sterilization wrap, surgical draping, surgical gowns, cover garments, such as over-suits, and the like.

21 Claims, 1 Drawing Sheet

U.S. PATENT DOCUMENTS

| | | | |
|---|---|---|---|
| 4,187,210 | 2/1980 | Howard, Jr. | 260/42.14 |
| 4,193,899 | 3/1980 | Brenner et al. | 260/23.5 |
| 4,197,150 | 4/1980 | Breidt, Jr. et al. | 156/229 |
| 4,209,563 | 6/1980 | Sisson | 428/288 |
| 4,303,708 | 12/1981 | Gebhardt et al. | 428/35 |
| 4,340,563 | 7/1982 | Appel et al. | 264/518 |
| 4,342,812 | 8/1982 | Selwood | 428/286 |
| 4,347,844 | 9/1982 | Ohki et al. | 128/287 |
| 4,350,655 | 9/1982 | Hoge | 264/145 |
| 4,364,985 | 12/1982 | Tokuyama et al. | 428/149 |
| 4,384,024 | 5/1983 | Mitchell et al. | 428/349 |
| 4,434,258 | 2/1984 | Schumacher et al. | 524/13 |
| 4,436,780 | 3/1984 | Hotchkiss et al. | 428/198 |
| 4,443,511 | 4/1984 | Worden et al. | 428/198 |
| 4,443,513 | 4/1984 | Meitner et al. | 422/195 |
| 4,467,595 | 8/1984 | Kramers | 57/225 |
| 4,472,328 | 9/1984 | Sugimoto et al. | 264/41 |
| 4,486,485 | 12/1984 | Sookne | 428/198 |
| 4,489,543 | 12/1984 | Bromley et al. | 57/208 |
| 4,515,854 | 5/1985 | Kogame et al. | 428/288 |
| 4,533,602 | 8/1985 | Nakamura et al. | 428/447 |
| 4,551,378 | 11/1985 | Carey, Jr. | 428/198 |
| 4,554,121 | 11/1985 | Kramers | 264/103 |
| 4,554,207 | 11/1985 | Lee | 428/288 |
| 4,578,307 | 3/1986 | Niki et al. | 428/288 |
| 4,585,604 | 4/1986 | Okuyama et al. | 264/41 |
| 4,606,964 | 8/1986 | Wideman | 428/152 |
| 4,606,970 | 8/1986 | Sharps, Jr. | 428/301 |
| 4,609,584 | 9/1986 | Cutler et al. | 428/156 |
| 4,612,148 | 9/1986 | Motooka | 264/49 |
| 4,613,643 | 9/1986 | Nakamura et al. | 524/426 |
| 4,652,487 | 3/1987 | Morman | 428/138 |
| 4,657,802 | 4/1987 | Morman | 428/152 |
| 4,668,566 | 5/1987 | Braun | 428/286 |
| 4,696,779 | 9/1987 | Wideman | 264/211.13 |
| 4,698,372 | 10/1987 | Moss | 521/145 |
| 4,704,238 | 11/1987 | Okuyama et al. | 264/41 |
| 4,720,415 | 1/1988 | Vander Wielen et al. | 428/152 |
| 4,734,324 | 3/1988 | Hill | 428/317.3 |
| 4,761,324 | 8/1988 | Rautenberg et al. | 428/198 |
| 4,767,580 | 8/1988 | Shingo et al. | 264/41 |
| 4,777,073 | 10/1988 | Sheth | 428/155 |
| 4,793,956 | 12/1988 | Nogiwa et al. | 264/41 |
| 4,794,128 | 12/1988 | Kawaguchi et al. | 521/138 |
| 4,801,494 | 1/1989 | Datta et al. | 428/283 |
| 4,814,124 | 3/1989 | Aoyama et al. | 264/41 |
| 4,822,350 | 4/1989 | Ito et al. | 604/372 |
| 4,824,718 | 4/1989 | Hwang | 428/284 |
| 4,829,096 | 5/1989 | Kitamura et al. | 521/79 |
| 4,879,078 | 11/1989 | Antoon, Jr. | 264/41 |
| 4,902,553 | 2/1990 | Hwang et al. | 428/156 |
| 4,906,513 | 3/1990 | Kebbell et al. | 428/198 |
| 4,919,738 | 4/1990 | Ball et al. | 156/73.5 |
| 4,921,653 | 5/1990 | Aoyama et al. | 264/41 |
| 4,923,650 | 5/1990 | Antoon, Jr. et al. | 264/41 |
| 4,929,303 | 5/1990 | Sheth | 156/209 |
| 4,981,747 | 1/1991 | Morman | 428/198 |
| 5,026,591 | 6/1991 | Henn et al. | 428/198 |
| 5,143,679 | 9/1992 | Weber et al. | 264/288.8 |
| 5,169,712 | 12/1992 | Tapp | 428/315.5 |
| 5,173,235 | 12/1992 | Kamei et al. | 264/154 |
| 5,176,953 | 1/1993 | Jacoby et al. | 428/315.5 |
| 5,188,885 | 2/1993 | Timmons et al. | 428/198 |
| 5,208,098 | 5/1993 | Stover | 428/284 |
| 5,229,191 | 7/1993 | Austin | 428/198 |
| 5,238,618 | 8/1993 | Kinzer | 264/41 |
| 5,238,623 | 8/1993 | Mrozinski | 264/48 |
| 5,238,636 | 8/1993 | Furukawa et al. | 264/41 |
| 5,244,482 | 9/1993 | Hassenboehler et al. | 55/528 |
| 5,260,360 | 11/1993 | Mrozinski et al. | 524/95 |
| 5,266,394 | 11/1993 | Diehl et al. | 428/261 |
| 5,332,613 | 7/1994 | Taylor et al. | 428/152 |
| 5,366,786 | 11/1994 | Connor et al. | 428/171 |
| 5,409,761 | 4/1995 | Langley | 428/198 |
| 5,415,925 | 5/1995 | Austin et al. | 428/287 |
| 5,431,643 | 7/1995 | Ouellette et al. | 604/385.1 |
| 5,437,653 | 8/1995 | Gilman et al. | 604/378 |
| 5,445,874 | 8/1995 | Shehata | 442/394 X |
| 5,467,765 | 11/1995 | Maturaporn | 128/206.19 |
| 5,470,639 | 11/1995 | Gessner et al. | 428/152 |
| 5,470,640 | 11/1995 | Modrak | 428/171 |
| 5,482,765 | 1/1996 | Bradley et al. | 428/286 |
| 5,484,645 | 1/1996 | Lickfield et al. | 428/198 |
| 5,492,751 | 2/1996 | Butt, Sr. et al. | 428/198 |
| 5,529,845 | 6/1996 | Branchesi et al. | 428/359 |
| 5,536,555 | 7/1996 | Zelazoski et al. | 428/138 |
| 5,540,976 | 7/1996 | Shawver et al. | 428/198 |
| 5,543,206 | 8/1996 | Austin et al. | 428/198 |
| 5,592,690 | 1/1997 | Wu | 442/394 X |
| 5,786,058 | 7/1998 | Megchelsen et al. | 428/57 |
| 5,865,919 | 2/1999 | Megchelsen et al. | 156/73.4 |

CLOTH-LIKE, LIQUID-IMPERVIOUS, BREATHABLE COMPOSITE BARRIER FABRIC

FIELD OF INVENTION

The present invention is directed to cloth-like, liquid-impervious, breathable composite barrier fabrics. More particularly, the present invention is directed to cloth-like, liquid-impervious, breathable film-nonwoven composite fabrics having biological liquid barrier capabilities for use as, for example, sterilization wrap, surgical draping, surgical gowns, cover garments, such as over-suits, and the like.

BACKGROUND OF THE INVENTION

Surgical gowns, surgical drapes, surgical face masks and sterile wrap and sterilization peel pouches (hereinafter collectively "surgical articles"), in order to function satisfactorily, must achieve a balance of properties, features and performance characteristics. Such surgical articles have, as a principal matter, been designed to greatly reduce, if not prevent, the transmission through the surgical article of biological liquids and/or airborne contaminates. In surgical procedure environments, such liquid sources include the gown wearer's perspiration, body fluids from the patient, such as blood, and life support liquids, such as plasma and saline. Examples of airborne contaminates include, without limitation, biological contaminates, such as bacteria, viruses and fungal spores. Such contaminates may also include particulate material such as, without limitation, lint, mineral fines, dust, skin squames and respiratory droplets. A measure of the barrier fabric's ability to prevent the passage of such airborne materials is sometimes expressed in terms of filtration efficiency.

Such surgical articles further should be comfortable during use, that is, while being worn. The breathability of the surgical article, that is, its rate of water vapor transmission, is an important measure of how comfortable a surgical article is to use. Other characteristics of surgical articles that impact upon the comfort of the article during use include, without limitation, the drapeability, cloth-like feel and hand and cool, dry feel of the articles.

Surgical articles also require a minimum level of strength and durability in order to provide the necessary level of safety to the user of the article, particularly during surgical procedures.

Finally, surgical articles desirably are inexpensive to manufacture, utilizing lightweight materials that enhance the comfort of the wearer during use, but also reduce the cost of such articles.

The use of liquid impervious, breathable multi-layer barrier fabrics of various constructions is known. Surgical articles formed from liquid repellent fabrics, such as fabrics formed from nonwoven webs or layers, have provided acceptable levels of liquid imperviousness, breathability, cloth-like drapeability, strength and durability, and cost. However, the need exists nonetheless for improved cloth-like, liquid-impervious, breathable barrier materials for use in forming surgical articles, as well as other garment and over-garment applications, such as personal protective equipment applications (i.e., workwear, for example), in which some or all of the above performance characteristics and features are desirable or necessary. Other personal protective equipment applications include, without limitation, laboratory applications, clean room applications, such as semiconductor manufacturing, agriculture applications, mining applications, environmental applications, and the like.

Moreover, personal care articles such as adult incontinent products and infant or child care diapers or garments such as training pants may utilize components with these desirable properties.

SUMMARY OF THE INVENTION

It is an object, therefore, of the present invention to provide an improved, cloth-like, liquid-impervious, breathable barrier material that achieves a unique balance of performance characteristics and features so as to be useful in garment, over-garment, and personal protective equipment applications, including as a surgical article.

It is, more specifically, an object of the present invention to provide an improved cloth-like, liquid-impervious, breathable barrier material that provides an effective barrier against passage of biological liquids, as measured by the requirements of ASTM ES 21 Test Procedure.

It is further an object of the present invention to provide an improved cloth-like, liquid-impervious, breathable barrier material that is very comfortable to the user when worn. The barrier material of the present invention exhibits a high level of breathability, as exemplified by a water vapor transmission rate (WVTR) of at least 1000 grams per square meter per 24 hours when measured in accordance with the test procedures described herein. The barrier material of the present invention further exhibits a textile-like drapeability, having a drape stiffness <4.0 centimeters when measured in accordance with the test procedures described herein.

It is yet another object of the present invention to provide an improved cloth-like, liquid-impervious, breathable barrier material that possesses suitable strength and durability for its intended use, having a grab tensile peak energy in the machine direction of at least about 15 inch-pounds force and in the cross-machine direction of at least about 19 inch-pounds force, and a peak strain in the machine direction of at least about 35 percent and in the cross machine direction of at least about 70 percent.

It is still another object of the present invention to provide an improved cloth-like, liquid-impervious, breathable barrier material that is lightweight and relatively inexpensive to manufacture, having a basis weight of less than about 2.0 ounces per square yard.

These and other objects are achieved by the improved cloth-like, liquid-impervious, breathable barrier material disclosed and claimed herein.

DETAILED DESCRIPTION OF THE INVENTION

Figure 1:
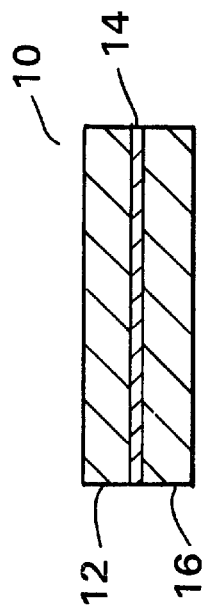
FIG. 1 is a cross-sectional view of the barrier material of the present invention.

The present invention is directed to an improved cloth-like, liquid-impervious, breathable barrier material, which possess a unique balance of performance characteristics and features making the material suitable for use in forming surgical articles, as well as other garment and over-garment applications, such as personal protective equipment applications. Referring to the drawings, an embodiment of the barrier material of the present invention is illustrated. The barrier material 10 is a laminate comprising three layers—a top nonwoven layer 12 formed, for example, of spunbond filaments, a bottom nonwoven layer 16 formed, for example, of spunbond filaments, and a middle breathable film layer 14 formed, for example, of a microporous film. The individual layers of barrier material 10 are laminated, bonded or attached together by known means, including thermal-mechanical bonding, ultrasonic bonding, adhesives, stitching and the like.

As used herein, the terms "layer" or "web" when used in the singular can have the dual meaning of a single element or a plurality of elements. As used herein, the term "laminate" means a composite material made from two or more layers or webs of material which have been bonded or attached to one another. As used herein, the terms "nonwoven fabric" or "nonwoven web" mean a web having a structure of individual fibers or filaments that are interlaid, but not in an identifiable, repeating manner as in a knitted or woven fabric.

Commercially available thermoplastic polymeric materials can be advantageously employed in making the fibers or filaments from which top nonwoven layer 12 and bottom layer 16 are formed. As used herein, the term "polymer" shall include, but is not limited to, homopolymer, copolymers, such as, for example, block, graft, random and alternating copolymers, terpolymers, etc., and blends and modifications thereof. Moreover, unless otherwise specifically limited, the term "polymer" shall include all possible geometric configurations of the material, including, without limitation, isotactic, syndiotactic, random and atactic symmetries. As used herein, the terms "thermoplastic polymer" or "thermoplastic polymeric material" refer to a long-chain polymer that softens when exposed to heat and returns to the solid state when cooled to ambient temperature. Exemplary thermoplastic materials include, without limitation, polyvinyl chlorides, polyesters, polyamides, polyfluorocarbons, polyolefins, polyurethanes, polystyrenes, polyvinyl alcohols, caprolactams, and copolymers of the foregoing.

Nonwoven webs that can be employed as the nonwoven layers 12 and 16 of the present invention can be formed by a variety of known forming processes, including spunbonding, airlaying, meltblowing, or bonded carded web formation processes. For example, in the embodiment of the present invention shown in the drawings herein, top layer 12 and bottom layer 16 are both spunbond nonwoven webs, which have been found advantageous in forming barrier material 10. Spunbond nonwoven webs are made from melt-spun filaments. As used herein, the term "meltspun filaments" refers to small diameter fibers and/or filaments which are formed by extruding a molten thermoplastic material as filaments from a plurality of fine, usually circular, capillaries of a spinneret with the diameter of the extruded filaments then being rapidly reduced, for example, by non-eductive or eductive fluid drawing or other well known spunbonding mechanisms. Lastly, the melt-spun filaments are deposited in a substantially random manner onto a moving carrier belt or the like to form a web of substantially continuous and randomly arranged, melt-spun filaments. Spunbond filaments generally are not tacky when they are deposited onto the collecting surface. The production of spunbond nonwoven webs is described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,538 to Peterson, and U.S. Pat. No. 3,542,615 to Dobo et al., all of which are incorporated herein by reference. The melt-spun filaments formed by the spunbond process are generally continuous and have average diameters larger than 7 microns based upon at least 5 measurements, and more particularly, between about 10 and 100 microns. Another frequently used expression of fiber or filament diameter is denier, which is defined as grams per 9000 meters of a fiber or filament.

Spunbond webs generally are stabilized or consolidated (pre-bonded) in some manner immediately as they are produced in order to give the web sufficient integrity and strength to withstand the rigors of further processing into a finished product. This pre-bonding step may be accomplished through the use of an adhesive applied to the filaments as a liquid or powder which may be heat activated, or more commonly, by compaction rolls. As used herein, the term "compaction rolls" means a set of rollers above and below the nonwoven web used to compact the web as a way of treating a just produced, melt-spun filament, particularly spunbond, web, in order to give the web sufficient integrity for further processing, but not the relatively strong bonding of later applied, secondary bonding processes, such as through-air bonding, thermal bonding, ultrasonic bonding and the like. Compaction rolls slightly squeeze the web in order to increase its self-adherence and thereby its integrity.

An exemplary secondary bonding process utilizes a patterned roller arrangement for thermally bonding the spunbond web. The roller arrangement typically includes a patterned bonding roll and a smooth anvil roll which together define a thermal patterning bonding nip. Alternatively, the anvil roll may also bear a bonding pattern on its outer surface. The pattern roll is heated to a suitable bonding temperature by conventional heating means and is rotated by conventional drive means, so that when the spunbond web passes through the nip, a series of thermal pattern bonds is formed. Nip pressure within the nip should be sufficient to achieve the desired degree of bonding of the web, given the line speed, bonding temperature and materials forming the web. Percent bond areas within the range of from about 10 percent to about 20 percent are typical for such spunbond webs.

Middle breathable film layer 14 can be formed of any microporous film that can be suitably bonded or attached to top and bottom layers 12, 16 to yield a barrier material 10 having the unique combination of performance characteristics and features described herein. A suitable class of film materials includes at least two basic components: a thermoplastic elastomeric polyolefin polymer and a filler. These (and other) components can be mixed together, heated and then extruded into a mono-layer or multi-layer film using any one of a variety of film-producing processes known to those of ordinary skill in the film processing art. Such film-making processes include, for example, cast embossed, chill and flat cast, and blown film processes.

Generally, on a dry weight basis, based on the total weight of the film, the film layer 14 will include from about 30 to about 60 weight percent of the thermoplastic polyolefin polymer, or blend thereof, and from about 40 to about 70 percent filler. Other additives and ingredients may be added to the film layer 14 provided they do not significantly interfere with the ability of the film layer to function in accordance with the teachings of the present invention. Such additives and ingredients can include, for example, antioxidants, stabilizers, and pigments.

In addition to the polyolefin polymer, the film layer 14 also includes a filler. As used herein, a "filler" is meant to include particulates and other forms of materials which can be added to the film polymer extrusion blend and which will not chemically interfere with the extruded film but which are able to be uniformly dispersed throughout the film. Generally, the fillers will be in particulate form and may have a spherical or non-spherical shape with average particle sizes in the range of about 0.1 to about 7 microns. Both organic and inorganic fillers are contemplated to be within the scope of the present invention provided that they do not interfere with the film formation process, or the ability of the film layer to function in accordance with the teachings of the present invention. Examples of suitable fillers include calcium carbonate ($CaCO_3$), various kinds of clay, silica ($SiO_2$), alumina, barium carbonate, sodium carbonate, magnesium carbonate, talc, barium sulfate, magnesium sulfate, aluminum sulfate, titanium dioxide ($TiO_2$), zeolites, cellulose-type powders, kaolin, mica, carbon, calcium oxide, magnesium oxide, aluminum hydroxide, pulp powder, wood powder, cellulose derivatives, chitin and chitin derivatives. A suitable coating, such as, for example, stearic acid, may also be applied to the filler particles.

As mentioned herein, film layer 14 may be formed using any one of the conventional processes known to those familiar with film formation. The polyolefin polymer and filler are mixed in appropriate proportions given the ranges outlined herein and then heated and extruded into a film. In order to provide uniform breathability as reflected by the water vapor transmission rate of the film, the filler should be uniformly dispersed throughout the polymer blend and, consequently, throughout the film layer itself. For purposes of the present invention, a film is considered "breathable" if it has a water vapor transmission rate of at least 300 grams per square meter per 24 hours ($g/m^2/24$ hours), as calculated using the test method described herein. Generally, once the film is formed, it will have a weight per unit area of less than about 80 grams per square meter (gsm) and after stretching and thinning, its weight per unit area will be from about 10 gsm to about 25 gsm.

The film layer used in the example of the present invention described below is a mono-layer film, however, other types, such as multi-layer films, are also considered to be within the scope of the present invention provided the forming technique is compatible with filled films. The film as initially formed generally is thicker and noisier than desired, as it tends to make a "rattling" sound when shaken. Moreover, the film does not have a sufficient degree of breathability as measured by its water vapor transmission rate. Consequently, the film is heated to a temperature equal to or less than about 5° C. below the melting point of the polyolefin polymer and then stretched using an in-line machine direction orientation (MDO) unit to at least about two times (2×) its original length to thin the film and render it porous. Further stretching of the film layer 14, to about three times (3×), four times (4×), or more, its original length is expressly contemplated in connection with forming film layer 14 of the present invention.

Film layer 14 after being stretch-thinned should have an "effective" film gauge or thickness of from about 0.2 mil to about 0.6 mil. The effective gauge is used to take into consideration the voids or air spaces in breathable film layers. For normal, non-filled, non-breathable films, the actual gauge and effective gauge of the film typically will be the same. However, for filled films that have been stretch-thinned, as described herein, the thickness of the film will also include air spaces. In order to disregard this added volume, the effective thickness is calculated according to the test method set forth herein.

Figure 2:
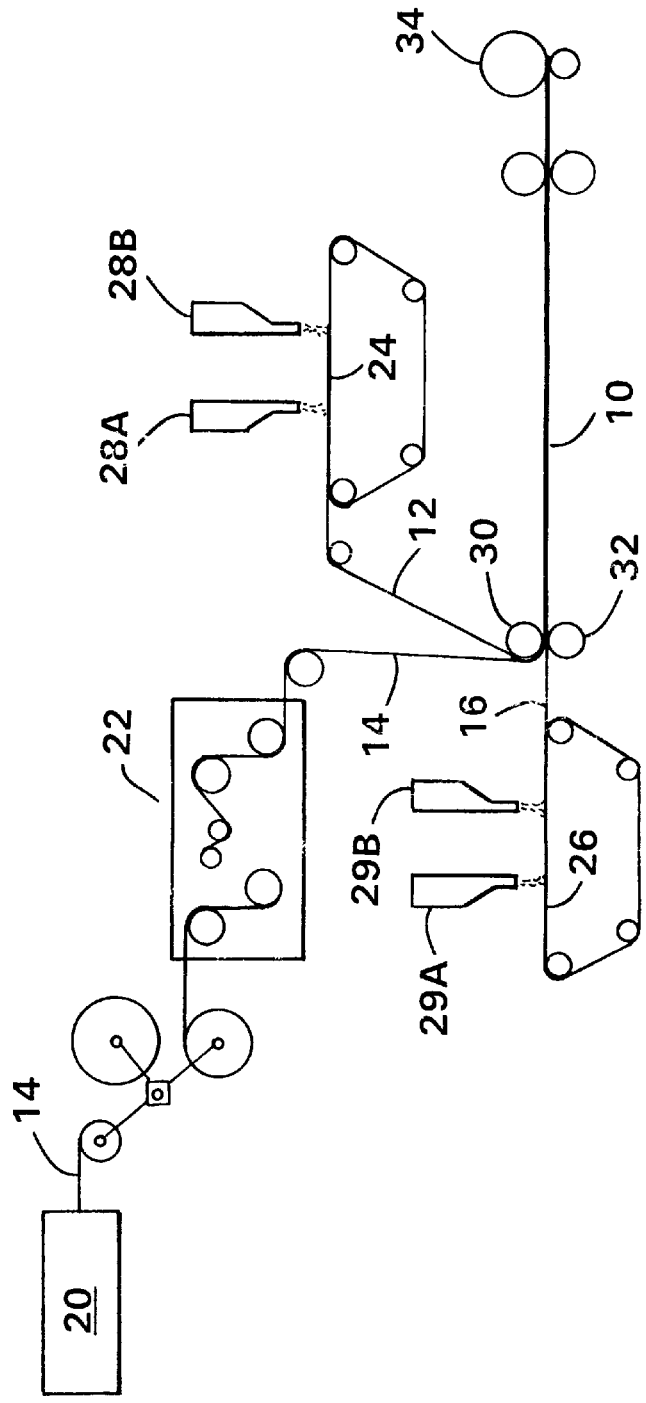
FIG. 2 is a schematic view of a process for making the barrier material of the present invention.

Referring now to FIG. 2, a process for continuously preparing a barrier material 10 according to the present invention is illustrated. The film layer 14 is formed using any type of conventional film forming equipment 20, such as cast or blown film equipment. The film layer 14 having a formulation as described herein then is passed through a film stretching apparatus 22 to stretch and thin the film to an effective gauge of 0.6 mil or less. One type of suitable film stretching apparatus is a Machine Direction Orienter unit, Model No. 7200, available from the Marshall & Williams Company, having offices in Providence, R.I.

While the film layer 14 is being stretched, the spunbond nonwoven layers 12 and 16 are formed. A conventional spunbond nonwoven webs manufacturing process, as described herein, can be used to form nonwoven layers 12 and 16. As shown in FIG. 2, the spunbond webs 12,16 are formed of substantially continuous and randomly arranged, melt-spun filaments, which are deposited onto moving continuous forming wires 24, 26 from extruders 28A, 28B, 29A, 29B. The webs of randomly arranged, melt-spun filaments then can be pre-bonded by passing each web 12, 16 through a pair of compaction rolls (not shown) to give the webs 12, 16 sufficient integrity and strength for further processing. One or both of the compaction rolls may be heated to aid in bonding the webs 12, 16. Typically, one of the compaction rolls also has a patterned outer surface that imparts a discrete bond pattern with a prescribed bond area to web 12 and/or web 16. The opposing compaction roll usually is a smooth anvil roll, although this roll also may have a patterned outer surface if desired.

Once the film layer 14 has been sufficiently stretch-thinned and oriented, and the spunbond webs 12,16 have been formed, the three layers are brought together and laminated to one another using a pair of laminating or bonding rolls 30, 32, as shown in FIG. 2, or other conventional bonding means, in order to produce the barrier material 10 of the present invention.

As shown in FIG. 2, bonding roll 30 is a pattern roll, whereas second bonding roll 32 is a smooth roll. Both rolls are driven by conventional means, such as, for example, electric motors (not shown). Pattern roll 30 is a right circular cylinder that may be formed of any suitable, durable material, such as, for example, steel, to reduce wear on the rolls during use. Pattern roll 30 has on its outermost surface a pattern of raised bonding area. An intermittent pattern of discrete, regularly repeating bonding points can be suitably employed, for example, as is conventional in the art. The bonding areas on pattern roll 30 form a nip with the smooth or flat outer surface of opposed positioned anvil roll 32. Which also is a right circular cylinder that can be formed of any suitable, durable material, such as, for example, steel, hardened rubber, resin-treated cotton or polyurethane.

The pattern of raised bonding areas on the pattern roll 30 is selected such that the area of at least one surface of the resulting barrier material 10 occupied by bonds after passage through the nip formed between pattern rolls 30, 32 ranges from about 10 percent to about 30 percent of the surface area of the barrier material. The bonding area of the barrier material 10 can be varied to achieve the above-mentioned percent bond area, as is known in the art.

The temperature of the outer surface of the pattern roll 30 can be varied by heating or cooling relative to the smooth roll 32. Heating and/or cooling can affect, for example, the degree of lamination of the individual layers forming the barrier material 10. Heating and/or cooling of pattern roll 30 and/or smooth roll 32 can be effected by conventional means (not shown) well known in the art. The specific ranges of temperatures to be employed in forming the barrier material 10 are dependent on a number of factors, including the types of polymeric materials employed in forming the individual layers of the barrier material 10, the dwell time of the individual layers within the nip and the nip pressure between the pattern roll 30 and anvil roll 32. After barrier material 10 exits the nip formed between bonding rolls 30, 32, the material 10 can be wound onto roll 34 for subsequent processing.

Modifications in the above-described process will be readily apparent to those of ordinary skill in the art without departing from the spirit and scope of the present invention. For example, after the barrier material 10 is formed, it can continue in-line for further processing and converting. Or, different apparatus can be used for stretch-thinning the film layer 14. Other known means for bonding and laminating the film layer 14 to nonwoven layers 12, 16 may be used, provided the resulting barrier material 10 has the required properties described herein. Finally, formation of the film layer 14 and/or nonwoven layers 12, 16 can take place at a remote location, with rolls of the individual layers unwound and fed to the nip formed between pattern roll 30 and smooth roll 32. Also, for certain applications, it is advantageous to have a two component material which can be formed as above described by omitting one of the spunbond webs, for example. Typical spunbond weights for such applications are between about 0.6 osy to about 1.5 osy, commonly between about 0.9 osy to about 1.3 osy. These materials may also be thermally or adhesively laminated to the stretch-thinned film to form the composite.

Having described certain embodiments of the present invention, a series of sample barrier materials were tested to further illustrate the present invention and to teach one of ordinary skill in the art the manner of carrying out the present invention. The results of the measurements of certain physical properties of the barrier materials so formed, and the test procedures used, are set forth below. For comparison purposes, measurements of these same physical properties were made for several commercially available barrier materials. The results reported are averages of values obtained, based upon five (5) measurements of each property for each sample and comparative barrier material.

Test Procedures

The following test procedures were used to analyze the sample and comparative barrier materials identified below.

Effective Gauge

The effective gauge of a film material was calculated by dividing the basis weight of the film by the density of the polymer(s) and fillers forming the film. To obtain the effective gauge of a film material in units of inches, the weight per unit area measured in ounces per square yard (osy) was multiplied by 0.001334 (a metric to English units conversion factor) and the result was divided by the density of the polymer formulation in grams per cubic centimeter (g/cc).

Tensile Strength and Elongation Tests The grab test for tensile strength and elongation measures the breaking load and percent elongation before rupture, i.e., the "stretchability" of a material. These measurements are made while the material is subjected to a continuously increasing load in a single direction at a constant rate of extension. This procedure closely conforms to ASTM Standards D-5035-92 and D-5035-92, and INDA IST 110.1-92, using a constant-rate-of-extension tensile testing machine, such as a Sintech System 2 Computer Integrated Testing System manufactured by MTS Systems Corporation of Eden Prairie, Minn.

For each sample material, five specimens were cut with a 4 inch (100 mm) wide precision cutter, with each having a width of 4 inches (100 mm) and a length of 6 inches (150 mm), with the long dimension parallel to the direction of testing and force application. The specimen was placed within clamps of the constant-rate-of-extension testing machine. The length or long dimension of each specimen was set as nearly parallel as possible to the direction of force application. A continuous load was applied to the specimen, with the crosshead speed (loading rate) set at 300 mm/minute, until the specimen ruptured. The peak load, peak energy and peak strain were recorded and average values are recorded herein. Measurements in the machine (MD) and cross machine (CD) directions were recorded separately.

Water Vapor Transmission Rate

The water vapor transmission rate (WVTR) for the sample materials was calculated in accordance with ASTM Standard E96-80. Circular samples measuring three inches in diameter were cut from each of the test materials and a control, which was a piece of CELGARD® 2500 film from Hoechst Celanese Corporation of Sommerville, N.J. CELGARD® 2500 film is a microporous polypropylene film. Three samples were prepared for each material. The test dish was a number 60-1 Vapometer pan distributed by Thwing-Albert Instrument Company of Philadelphia, Pa. One hundred milliliters (ml) of distilled water was poured into each Vapometer pan and individual samples of the test materials and control material were placed across the open tops of the individual pans. Screw-on flanges were tightened to form a seal along the edges of each pan (no sealant grease was used), leaving the associated test material or control material exposed to the ambient atmosphere over a 6.5 centimeter (cm) diameter circle having an exposed area of approximately 33.17 square centimeters. The pans were weighed, then were placed in a forced air oven set at a temperature of 37° C. The oven was a constant temperature oven with external air circulating through it to prevent water vapor accumulation inside. A suitable forced air oven is, for example, a Blue M Power-O-Matic 60 oven distributed by Blue M Electric Co. of Blue Island, Ill. After 24 hours, the pans were removed from the oven and weighed again. The preliminary test water vapor transmission rate values were calculated as follows:

Test WVTR=(grams weight loss over 24 hours)×315.5 (g/m$^2$/24 hrs)

The relative humidity within the oven was not specifically controlled.

Under predetermined set conditions of 100° F. (32° C.) and ambient relative humidity, the WVTR for the CELGARD® 2500 film control has been determined to be 5000 grams per square meter for 24 hours (g/m$^2$/24 hrs). Accordingly, the control sample was run with each test and the preliminary test values were corrected to set condition using the following equation:

WVTR=(Test WVTR/control WVTR)×5000 g/m$^2$/24 hrs (g/m$^2$/24 hrs)

Basis Weight

The basis weights of sample materials were determined in accordance with Federal Test Method No. 191A/5041. Sample size for the sample materials was 15.24×15.24 centimeters and five values were obtained for each material and then averaged.

Hydrostatic Pressure Test

The hydrostatic pressure test measures the resistance of nonwoven materials to the penetration of water under low hydrostatic pressure. This test procedure is in accordance with Method 5514—Federal Test Methods Standard No. 191A, AATCC Test Method 127-89 and INDA Test method 80.4-92, modified to include a screen support of standard synthetic fiber window screen material.

The test head of a Textest FX-300 Hydrostatic Head Tester, available from Schmid Corp., having offices in Spartanburg, S.C. was filled with purified water. The purified water was maintained at a temperature between 65° F. and 85° F. (18.3 and 29.4° C.), which was within the range of normal ambient conditions (about 73° F. (23° C.) and about 50% relative humidity) at which this test was conducted. An 8 inch×8 inch (20.3 cm×20.3 cm) square sample of the test material was placed such that the test head reservoir was covered completely. The sample was subjected to a standardized water pressure, increased at a constant rate until leakage was observed on the outer surface of the sample material. Hydrostatic pressure resistance was measured at the first sign of leakage in three separate areas of the sample. This test was repeated for five specimens of each sample material. The hydrostatic pressure resistance results for each specimen were averaged and recorded in millibars. A higher value indicates greater resistance to water penetration.

Cup Crush Test

The cup crush test is used to measure the softness of a material by using the peak load and energy units from a constant-rate-of-extension tensile testing machine. The lower the peak load value, the softer the material.

This test procedure was conducted in a controlled environment wherein the temperature was about 73° F. (23° C.) and the relative humidity was about 50 percent. Samples were tested using a Sintech System 2 Computer Integrated Testing System as described herein, and a Crush Test Stand available from Kimberly-Clark Corp. Quality Assurance Department in Neenah, Wis. which included a model 11 foot, a model 31 steel ring, a base plate, a model 41 cup assembly, and a calibration set.

The steel ring was placed over the forming cylinder and a 9 inch×9 inch (22.9 cm×22.9 cm) sample was centered over the forming cylinder. The forming cup was slid over the forming cylinder until the sample was pinched between the forming cylinder and the steel ring all the way around the steel ring. The forming cup was placed on top of the base plate of the load cell and firmly seated over the ridge of the base plate. The foot was mechanically lowered into the forming cup with the crosshead speed set at 400 millimeters per minute, crushing the sample while the constant-rate-of-extension tensile testing machine measured the peak load in grams and the energy in gram-mm needed to crush the sample. The average values for peak load and energy for five specimens from each sample material were calculated and reported herein.

Drape Stiffness Test

The drape stiffness test determines the bending length of a fabric using the principle of cantilever bending of the fabric under its own weight. This test method measures the drape stiffness or resistance to bending of the fabric. Bending length is a measure of the interaction between fabric weight and fabric stiffness as shown by the way in which a fabric bends under its own weight. This is a reflection of the stiffness of the fabric when bent in one plane under the force of gravity.

A 1 inch by 8 inch (2.54 cm by 20.32 cm) specimen was slid, at 4.75 inches per minute (12.07 cm per minute), in a direction parallel to its long dimension, so that its leading edge projected from the edge of a horizontal surface. The length of the overhang was measured when the tip of the specimen depressed under its own weight to the point where the line joining the tip to the edge of the platform made a 41.5° angle with the horizontal. The longer the overhang, the slower the fabric was to bend; thus, higher numbers indicate a stiffer fabric.

This test procedure conformed to ASTM Standard Test D 1388, except for the specimen size as noted herein. MD and CD measurement of bending length were made and recorded separately. A cantilever bending tester was used, such as Model 79-10 available from Testing Machines, Inc., having offices in Amityville, N.Y.

The drape stiffness was calculated as follows:

$$\text{Drape stiffness (cm)} = \text{bending length (inches)} \times 2.54$$

Average values of drape stiffness are recorded herein.

EXAMPLES

Sample 1

A barrier material according to the present invention was made. The film layer contained, on a total weight percent basis based upon the weight of the film, 13% Shell 6D82 polypropylene/polyethylene copolymer with 5.5% ethylene content, 18% Rexene FD-D1700 low crystallinity polypropylene having atactic stereoisomers in a high molecular weight polymer chain, 3% Dow 5004 with 60,000 ppm Irgafos 168 used as an antioxidant and stabilizer, 2% SCC 12673 blue color concentrate available from Standridge Color Corp., and 64% English China Supercoat calcium carbonate ($CaCO_3$) coated with 1½% behenic acid, having a 1 micron average particle size and a top cut of 7 microns. The calcium carbonate was obtained from ECCA Calcium Products, Inc. in Sylacauga, Ala., a division of ECC International. The film formulation was blown into a mono-layer film.

The spunbond facing layers were both 0.60 ounces per square yard nonwoven webs formed from extrudable thermoplastic resins of 97% Shell 6D43 random copolymer of propylene and ethylene monomers containing 3% ethylene, 2% titanium dioxide (white), 0.09% anti-static compound and 0.91 SCC 11111 blue color concentrate. The spunbond filaments were essentially continuous in nature and had an average fiber size of 2.0 dpf.

The film and nonwoven layers were laminated together using thermal bonding rolls, as described herein. The pattern roll had a bonding temperature of about 185° F. and the smooth anvil roll had a temperature of about 145° F. The nip pressure formed between the rolls was about 440 psig.

Comparative Sample 2

A commercially available Baxter Vira Block surgical gown was tested.

Comparative Sample 3

A commercially available 3M Surgical Gown with Prevention fabric was tested.

Comparative Sample 4

A commercially available Baxter Optima standard surgical gown was tested.

Comparative Sample 5

A commercially available Kimberly-Clark Corp. Evolution 3 standard surgical gown was tested.

All measurements shown in the following tables were taken from the body of the respective surgical gowns. All values shown are average values, based upon five measurements.

TABLE I

| SAMPLE | BASIS WEIGHT (osy) | MD PEAK LOAD (lb) | GRAB PEAK ENERGY (in-lb) | TENSILE PEAK STRAIN (%) | CD PEAK LOAD (lb) | GRAB PEAK ENERGY (in-lb) | TENSILE PEAK STRAIN (%) |
|---|---|---|---|---|---|---|---|
| 1 | 1.844 | 23.015 | 15.605 | 39.306 | 16.676 | 19.073 | 71.458 |
| 2 | 2.681 | 28.451 | 14.877 | 34.746 | 21.507 | 16.216 | 54.796 |
| 3 | 1.822 | 29.929 | 30.191 | 57.490 | 22.995 | 29.697 | 70.650 |
| 4 | 2.239 | 27.332 | 12.174 | 28.230 | 15.763 | 17.164 | 77.252 |
| 5 | 1.579 | 19.648 | 13.237 | 37.172 | 14.844 | 12.486 | 51.040 |

TABLE II

| SAMPLE | HYDROHEAD (mbar) | WVTR (g/m²/24 hrs) | CUP ENERGY (g/mm) | CRUSH LOAD (grams) | DRAPE MD (cm) | STIFFNESS CD (cm) |
|---|---|---|---|---|---|---|
| 1 | 250.00 | 3,019.45 | 2,940.12 | 163.99 | 3.580 | 2.240 |
| 2 | 250.00 | 1,628.82 | 4,975.54 | 284.27 | 3.890 | 3.020 |
| 3 | 250.00 | 4,308.00 | 3,829.26 | 189.16 | 2.190 | 2.230 |
| 4 | 26.6 | 4,846.97 | 5,514.46 | 317.65 | 4.100 | 2.180 |
| 5 | 54.6 | 4,861.78 | 2,954.77 | 154.94 | 3.370 | 2.520 |

The data shown in Tables I and II clearly illustrate that the barrier material 10 of the present invention achieves a unique combination of physical characteristics and properties in terms of low basis weight, good strength and durability, barrier properties, breathability, and textile-like drape and softness.

It is contemplated that the improved cloth-like, liquid-impervious, breathable barrier material constructed in accordance with the present invention will be tailored and adjusted by those of ordinary skill in the art to accommodate various levels of performance demand imparted during actual use. Accordingly, while this invention has been described by reference to certain specific embodiments and examples, it will be understood that this invention is capable of further modifications. This application is, therefore, intended to cover any variations, uses or adaptations of the invention following the general principles thereof, and including such departures from the present disclosure as come within known or customary practice in the art to which this invention pertains and fall within the limits of the appended claims.

We claim:

1. A cloth-like, liquid-impervious, breathable barrier material comprising:
   at least one nonwoven layer,
   a microporous, film layer comprising about 40 to about 70% filler by weight and about 30% to about 60% of a polyolefin polymer, or blend thereof and having a thickness of 0.5 mil or less bonded to said nonwoven layer to form a laminate, said laminate being breathable as measured by WVTR of at least 1,000 gm/m²/day and having a basis weight of about 2.0 ounces per square yard or less, a peak energy in the machine direction of at least 15 inch-pounds, a peak strain in the machine direction of at least about 35 percent, a peak energy in the cross machine direction of at least about 19 inch-pounds, a peak load in the cross machine direction of at least about 19 inch-pounds, a peak strain in the cross machine direction of at least about 70 percent, a hydrohead of about 250 mbars or more, a cup crush peak load of less than about 180 grams and a cup crush energy of less than about 3,000 grams per millimeter, a drape stiffness in the machine direction of <4.0 centimeters and a drape stiffness in the cross machine direction of <3.0 centimeters.

2. The cloth-like, liquid-impervious, breathable barrier material of claim 1 further comprising first and second nonwoven layers.

3. The cloth-like, liquid-impervious, breathable barrier material of claim 1 wherein said nonwoven layer comprises a spunbond web.

4. The cloth-like, liquid-impervious, breathable barrier material of claim 2 wherein said first and second nonwoven layers comprise first and second spunbond webs.

5. The cloth-like, liquid-impervious, breathable barrier material of claim 1 wherein said film layer is a mono-layer film.

6. The cloth-like, liquid-impervious, breathable barrier material of claim 1 wherein said film layer is a multi-layer film.

7. The cloth-like, liquid-impervious, breathable barrier material of claim 1 wherein said laminate has a water vapor transmission rate of at least about 3000 grams per square meter per 24 hours.

8. The cloth-like, liquid-impervious, breathable barrier material of claim 1 wherein said nonwoven layer comprises about 98% random copolymer of polypropylene and polyethylene with 3% ethylene content.

9. The cloth-like, liquid-impervious, breathable barrier material of claim 1 consisting essentially of one nonwoven layer and one film layer.

10. A surgical gown comprising the cloth-like, liquid-impervious, breathable barrier material of claim 1.

11. A surgical gown comprising the cloth-like, liquid-impervious, breathable barrier material of claim 9.

12. A surgical drape comprising the cloth-like, liquid-impervious, breathable barrier material of claim 1.

13. A surgical drape comprising the cloth-like, liquid-impervious, breathable barrier material of claim 9.

14. A sterilization peel pouch comprising the cloth-like, liquid-impervious, breathable barrier material of claim 1.

15. A sterilization peel pouch comprising the cloth-like, liquid-impervious, breathable barrier material of claim 9.

16. An industrial protective garment comprising the cloth-like, liquid-impervious, breathable barrier material of claim 1.

17. An industrial protective garment comprising the cloth-like, liquid-impervious, breathable barrier material of claim 9.

18. The cloth-like, liquid-impervious, breathable barrier material of claim 1 comprising a thermoplastic elastomeric polyolefin.

19. The cloth-like, liquid-impervious, breathable barrier material of claim 9 comprising a thermoplastic elastomeric polyolefin.

20. A personal care article comprising the cloth-like, liquid-impervious, breathable barrier material of claim 1.

21. A personal care article comprising the cloth-like, liquid-impervious, breathable barrier material of claim 9.

* * * * *